United States Patent [19]

Preziosi et al.

[11] 4,373,032

[45] Feb. 8, 1983

[54] METAL SALTS OF POLYACETYLENIC COMPOUNDS AND USES THEREOF AS ION EXCHANGE AND THERMOCHROMIC POLYMERS

[75] Inventors: Anthony F. Preziosi, Ledgewood; Gordhanbhai N. Patel, Morris Plains; Robert G. Denkewalter, Westfield; Ray H. Baughman, Morris Plains, all of N.J.

[73] Assignee: Allied Corporation, Morris Township, Morris County, N.J.

[21] Appl. No.: 159,741

[22] Filed: Jun. 16, 1980

[51] Int. Cl.³ .................. C08F 38/02; B01J 39/20; C08F 2/46
[52] U.S. Cl. .......................... 521/38; 526/285; 204/159.22
[58] Field of Search ............ 526/355; 521/38; 204/159.22

[56] References Cited

U.S. PATENT DOCUMENTS

| | | | |
|---|---|---|---|
| 3,501,302 | 3/1970 | Foltz | 96/88 |
| 3,999,946 | 12/1976 | Patel et al. | 23/253 |
| 4,215,208 | 7/1980 | Yee et al. | 526/285 |
| 4,235,108 | 11/1980 | Patel | 204/159.22 |
| 4,238,352 | 12/1980 | Patel | 204/159.22 |
| 4,314,021 | 2/1982 | O'Brien et al. | 204/159.22 |

FOREIGN PATENT DOCUMENTS 21695 of 1881 United Kingdom ........... 204/159.22

OTHER PUBLICATIONS

Journal of Polymer Science, vol. 16, No. 11, pp. 607–614, Polymers Letters ed., Patel, et al.
B. Tieke, et al., Journal of Polymer Science, Pol. Chem. Ed., vol. 17 1631–1644, 1979, John Wiley and Sons.

*Primary Examiner*—Joseph L. Schofer
*Assistant Examiner*—Peter F. Kulkosky
*Attorney, Agent, or Firm*—Kenneth E. Stroup, Jr.; Alan M. Doernberg

[57] ABSTRACT

Water-soluble polyacetylenic alkali metal salts from monomers and polymers of carboxymethyl urethanes of di-, tetra-, and hexayne diols, or from the corresponding diacids; useful in thermal and irradiation exposure indicators and/or in detection and/or removal of nonalkali metal ions dissolved in aqueous media.

12 Claims, No Drawings

METAL SALTS OF POLYACETYLENIC COMPOUNDS AND USES THEREOF AS ION EXCHANGE AND THERMOCHROMIC POLYMERS

BACKGROUND OF THE INVENTION

In the Journal of Polymer Science: Polymer Letters Edition, Volume 16 of 1978, pages 607–614 G. N. Patel et al. describe polymers of certain alpha, omega diacetylene bis(butoxycarbonylmethyl urethanes) and analogous ethoxy compounds; which, unlike theretofore known polydiacetylenic compounds, are substantially soluble in certain common organic solvents. Such solutions are remarkable in showing dramatic color changes when a nonsolvent is added.

SUMMARY OF THE INVENTION

This invention relates to water-soluble polyacetylenic polymers, which are alkali metal salts, or the corresponding acids, derived from the abovementioned polyacetylenic polymers and from related polymers; and to the alkali metal salts or acids of the corresponding monomers. The water-soluble polyacetylenic polymers of the invention are useful for detection and removal of certain metal ions from aqueous solutions; and the monomers and polymers can be used in time/temperature indicating devices wherein the monomer is activated by conversion to acid form to undergo a change in color or shade by contact with a reagent; or the polymer in acid form undergoes a color change when converted to the salt form by a reagent such as an aqueous alkali permeating a microporous membrane, separating said polymer and said reagent, at a rate which varies with temperature.

The polymers of the invention are polyacetylenes of the group corresponding to the monomeric formula $[R(C{\equiv}C)_a(CH_2)_b(C{\equiv}C)_{b-1}]_2$, a being 1 or 2, and b being 0 when a is 1 and b being 0, 1 or 2 when a is 2 and $(b-1)$ being taken as zero whenever b is zero; wherein R is selected from the group consisting of (I); $-(CH_2)_nO(C{\equiv}O)NHCH_2CO_2M'$, n being an integer from 1 to 10 and M representing an alkali metal or hydrogen; and (II); $-(CH_2)_{n'}CO_2M'$, n' being an integer from 0 to 9 and M' being an alkali metal.

More especially polymers of the invention conform to the formulas above wherein a is 1, b and $(b-1)$ are zero, and R is of formula I wherein n is 3 or 4; and more especially such polymers wherein M is potassium or sodium.

For applications such as removal of metal ions from aqueous solution, the polymer salt of the invention can be a cross-linked or a noncrosslinked polymer. Such polymer exchanges its alkali metal ion for ions of other metals in aqueous solution whereupon the salt of said polymer with such other metal precipitates from said aqueous solution.

DETAILED DESCRIPTION

The reactions were carried out in the laboratory in 1 L glass 3-necked flasks fitted with a mechanical stirrer, thermometer, an addition funnel, and an inlet and an outlet tube to allow blanketing the system with nitrogen or admitting a stream of oxygen.

The diols were prepared by oxidatively coupling the appropriate mono-ols using the Hay method (J. Pol. Sci, vol. 7 of 1960 pg. 1625). Briefly, to a solution consisting of 350 mL methanol, 6 g cuprous chloride, and 12 mL N,N,N',N'-tetramethylethylenediamine (TMEDA), a solution composed of 100 g mono-ol mixed with 50 mL methanol was added dropwise for a period of 0.75 to 1.0 h. Oxygen was bubbled into the reaction medium at a moderate rate throughout the duration of the run; between 8 and 16 h. were ample. Afterwards the solvent was stripped and the residue acidified with 5 N hydrochloric acid. The diol was extracted with diethylether, washed with water, neutralized with sodium bicarbonate, dried with anhydrous magnesium sulfate, then stripped of its solvent. Crystallization of the product was obtained by extracting the viscous residue with a 4:1 combination of xylene and heptane followed by refrigeration. The solid that formed was filtered and the recrystallization repeated (a mixture of diethyl ether and petroleum ether may be used for the dodecadiyn diol). Conversions to the diols were usually in excess of 80%.

The 4,6-decadiyn-1, 10-diol is a white fluffy solid that changes to blue in daylight; M.P. 44.8°–45.7° C. The 5,7-dodecadiyn-1,12-diol is a white particulate solid, unreactive to U.V. radiation; M.P. 50.1°–50.7° C.

Conversion of diols to diacids was accomplished using chromic acid solution as an oxidizer, prepared by mixing 35 g $CrO_3$ with 175 mL water and while stirring the solution in an ice-bath, adding incrementally 56 g concentrated sulfuric acid so as to minimize the exothermic reaction due to the heat of mixing.

The various product melting points (uncorrected) were obtained on a hot-stage melting point apparatus, observed through a microscope.

The IR spectra were recorded on a spectrophotometer by forming KBr pellets of the products.

Microanalytic techniques were used for the elemental analyses.

EXAMPLE 1

Synthesis of 4,6-Decadiyn-1,10-Dioic Acid $[HOCO(CH_2)_2C{\equiv}C]_2$

To a solution of 16.6 g (0.1 mol) 4,6-decadiyn-1,10-diol and 175 mL acetone, chromic acid was added dropwise over a period of 0.75 h. The temperature was maintained between 15° and 25° C. using a solid $CO_2$/acetone bath. (Caution: care must be exercised to avoid an extreme exotherm during the addition). After 0.25 h. the bath was removed and the reactants allowed to react for an additional 3 h.

The solution was extracted 3 times with diethylether using 150 mL each time. The combined extract was condensed to 300 mL and 150 mL 2.5 N NaOH was added while stirring to form the disodium salt. The aqueous layer was separated and saved. The ether layer was extracted with 100 mL water which was combined with the previous aqueous layer. The aqueous phase was then back extracted with three portions, 50 mL each, of diethylether. The aqueous portion was chilled in a cold water bath and neutralized by slowly adding a 5 N hydrochloric acid solution to regenerate the diacid; the end-point being noted by product precipitation. The product was recrystallized by dissolving in 200 mL hot ethylacetate followed by 75 mL xylene and refrigeration at −26° C.

After crystallization the product was filtered, washed with xylene followed by petroleum ether (60°–110°) and vacuum dried. Yield; 7.5 g of white solid which turns red slowly under U.V. light. Decomposes, 225°–230° C.

Elemental Analysis: Calcd. for $C_{10}H_{10}O_4$: C, 61.85; H, 5.19, O, 32.96. Found: C, 61.67, H, 4.95; O, 33.21.

IR Analysis: (bonded OH of the acid), 3,300 and 2,500; (C≡C), 2,240(w); (carbonyl) 1,700(s); (C—O stretch), 1,300(s) and 1,200 cm$^{-1}$.

EXAMPLE 2

Synthesis of 5,7-Dodecadiyn-1,12-Dioic Acid [HOCO(CH$_2$)$_3$C≡C]$_2$

The same general procedure was followed except that 19.4 g (0.1 mol) 5,7-dodecadiyn-1,12-diol was used as the starting material.

The diacid product was recrystallized by dissolution in 200 mL diethylether followed by separation to segregate the residual water present, and addition of 300 mL petroleum ether (60°–110°) to precipitate the product. The product was filtered, washed several times with petroleum ether and dried. Yield: 17.5 g of pink powdery solid. Decomposes, 225°–230° C. The product was both U.V. and thermally active; noted by its turning red at a moderate rate in daylight and at a slower rate when protected from light sources even when refrigerated.

ANALYSIS: Elemental: Calcd. for $C_{12}H_{14}O_4$: C, 64.85; H, 6.35; O. 28.80. Found: C, 66.02; H, 6.62; O, 27.45.

IR: (bonded-OH of the acid), 3,200 and 2,500; (C≡C), 2,240(w); (carbonyl), 1,700(s); (—(CH$_2$)$_3$), 1,458; (C—O) stretch) 1,270 and 1,210 cm$^{-1}$.

EXAMPLE 3

(A) Synthesis of 4,6-Decadiyn-1,10-Bis(Butoxycarbonylmethyl Urethane)

To a solution of 20.0 g (0.12 mol) 4,6-decadiyn-1,10-diol, 250 mL tetrahydrofuran (THF), and 0.2 g dibutyltin-di-2-ethylhexanoate dissolved in 4 mL triethylamine, a solution consisting of 56.6 g (0.36 mol) butyl isocyanatoacetate ($C_4H_9OCOCH_2NCO$) dissolved in 50 mL THF was added dropwise over a period of 0.5 h. After 3 hours the product, having formula [$C_4H_9OCOCH_2NHCOO(CH_2)_3C≡C—$]$_2$, was precipitated with heptane and recrystallized in 700 mL isopropyl ether. Yield: 51.0 g (90.4% of theoretical) of white fluffy solid which turns blue slowly. M.P. 64.2°–64.7° C.

(B) Synthesis of 4,6-Decadiyn-1,10-Bis(Carboxylmethylurethane)

24.0 g (0.05 mol) of the above 4,6-decadiyn-1,10-bis(-butoxycarbonylmethyl urethane) was converted to its dipotassium salt in aqueous solution by adding it incrementally to 250 mL of a 1.25 N KOH solution consisting of a 1:1 mixture of ethanol and water; the ester phase dissolved immediately. The mixture was heated below its boiling point while stirring for 2 hrs.

The solution was allowed to cool and was acidified with 300 mL of 3 N HCl, precipitating a white solid. The product was filtered and washed several times with water. The product was recrystallized by dissolving it in 300 ml methanol followed by 100 ml petroleum ether (30°–65° C.). The product was precipitated by refrigerating at −26° C.

The precipitated product was filtered, washed several times with petroleum ether (55°–60° C.) and dried in a vacuum oven. Yield, 14.8 g (0.040 mole) of fluffy white solid that turns blue in daylight after a short period of time. M.P. 177°–179° C.

ANALYSIS: Calcd. for $C_{16}H_{20}N_2O_8$: C, 52.17; H, 5.47; N, 7.61; O, 34.75. Found: C, 52.63; H, 5.33; N, 7.38; O, 34.66.

IR Analysis: Urethane: (NH stretch), 3,320; (COO or amide I), 1690; (NH, CN or amide II), 1,550 cm$^{-1}$. Acid: (carbonyl), 1,705; (C—O of acid), 1240 cm$^{-1}$.

(C) Preparation of Poly-4,6-Decadiyn-1,10-Bis(Butyoxycarbonylmethyl Urethane) by Gamma-Ray Radiation 20.0 g of 4,6-decadiyne-1,10-bis(butoxycarbonylmethyl urethane) recrystallized from 350 mL isopropylether to a white crystalline product was polymerized by $^{60}Co$ γ-ray radiation of 50 Mrad at a dose rate of 1 Mrad per hour. The metallic green trans-1,4-polymerized product was extracted twice in boiling acetone followed by filtration and washings with unheated acetone and dried. Yield; 9.5 g of fine textured metallic green product.

(D) Saponification of Poly-4,6-Decadiyn-1,10-Bis(Butoxycarbonylmethyl Urethane) to the Potassium Salt of the Diacid The butyl end group was cleaved by dissolving 9.0 g of the above poly(4,6-decadiyn-1,10-bis(butoxycarbonylmethyl urethane)) in 200 mL chloroform. A solution consisting of 5.5 g KOH dissolved in 200 mL methanol was added slowly while stirring. The product which was allowed to precipitate over several days was filtered, washed with ethanol, and dried in a vacuum oven at 60° C. for 16 hours. Yield; 11.1 g. (The higher than expected yield is due to water of hydration).

(E) Crosslinking of the Potassium Salt of Poly-4,6-Decadiyn-1,10-Bis(Carboxylmethyl Urethane) by γ-Ray Radiation in Solution A 7.0 g samples of the potassium salt of the poly-4,6-decadiyn-1,10-bis(carboxylmethyl urethane) product of Part (D) of this Example was dissolved in 700 mL distilled water by stirring the mixture for at least 16 hours. The reddish semiviscous solution was set in 3 bottles and exposed to 50 Mrad $^{60}Co$ γ-ray radiation at a dose rate of 1 Mrad per hour. The pH of the resulting aqueous products ranged from 7.2 to 7.4. The final aqueous products were not viscous, thus indicating that the product was a crosslinked, water-insoluble polymer in aqueous suspension.

These suspensions, and also solutions of noncrosslinked polymer salt, were tested individually with aqueous solutions of various cations including $Ag^+$, $Al^{3+}$, $Ba^{2+}$, $Cd^{2+}$, $Co^{2+}$, $Hg^{2+}$, $Mn^{2+}$, $Pb^{2+}$, $Sn^{4+}$, $Sr^{2+}$, $Zn^{2+}$, $Fe^{2+}$, $Fe^{3+}$, $Cu^{2+}$, $Ca^{2+}$, $Mg^{2+}$, $Cr^{2+}$, $Cr^{3+}$, and $Ni^{2+}$. All of these metal cations caused precipitation. Accordingly, these crosslinked and noncrosslinked polymers can be used to separate metallic cation impurities, other than alkali metal cations, from water. The metal can be recovered via contacting aqueous acid with the polymeric precipitate, forming an aqueous solution of the metal salt of the acid, which can be separated from the polymeric residue. The alkali metal salt of the polymer can be regenerated as its aqueous solution or dispersion by addition thereto of aqueous alkali. Sodium and also lithium as the cation gives similar results to those obtained using potassium cation in the above Example.

EXAMPLE 4
Recovery of Metals from the Resin

The general scheme for preparation of the "split" higher acetylenic acids is as follows, wherein each compound is numbered under its formula:

SCHEME 1

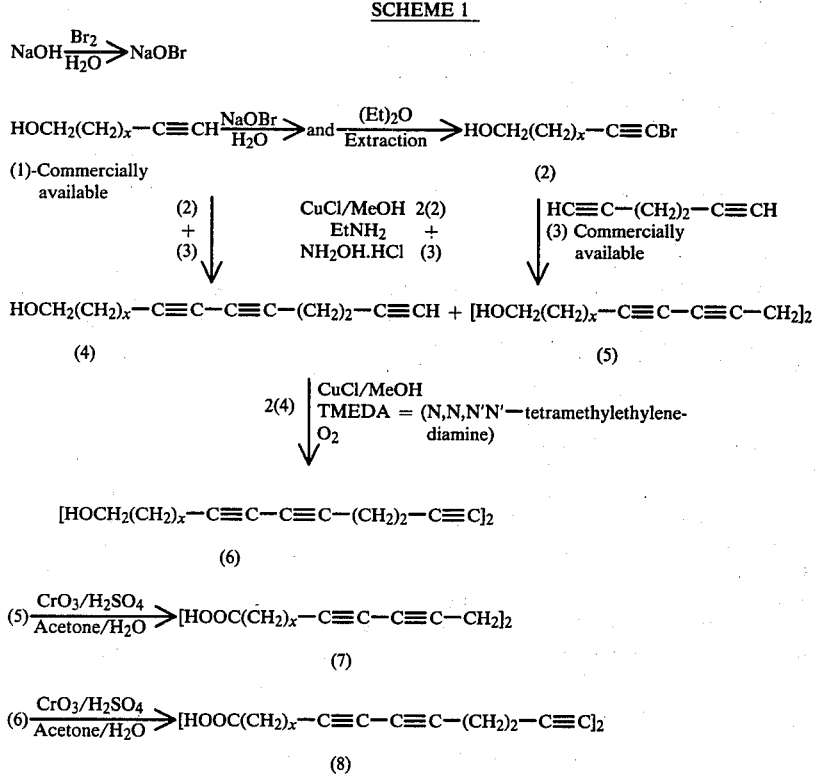

Step 1: In 5 mL of 0.1% solution of the potassium salt of Example 3D in water was added dropwise an aqueous solution of $FeCl_3$ till the polymer precipitated. The red precipitates were filtered, washed several times with distilled water and collected. The first filtrate was titrated with KSCN solution. No red precipitates were detected. (K has exchanged with $Fe^{3+}$).

Step 2: When the red precipitates were placed in about 0.1 N HCl, the precipitates turned black-violet. The filtrate was titrated with KSCN. The filtrate turned red, indicating $Fe^{3+}$ had passed into the aqueous acid and was replaced by $3H^+$ in the polymer.

Step 3: To the dark violet residues, 0.1 N KOH solution in water was added. The residues dissolved to form yellow solution. This polymer solution can be recycled to step 1.

WATER SOLUBLE MONOMERS FROM HIGHER ACETYLENES

Additional water soluble monomers were prepared by converting the diols of higher acetylenes (acetylenes having more than two acetylenic groups) to their dicarboxylic acid alkali metal salts. Some of these compositions (designated as "split" tetraynes and hexaynes) have the ethylene radical —($CH_2CH_2$)— in the backbone, in accordance with the formula: $[M'O(C=O)(CH_2)_{n'}(C\equiv C)_2(CH_2)_b(C\equiv C)_{b-1}]_2$ where b is 1 or 2, n' being an integer from 1 to 4 and M' being an alkali metal, whereas others have a fully conjugated backbone, in accordance with the formula: $[M'O(C=O)(CH_2)_{n'}(C\equiv C)_2]_2$.

SPECIFIC PROCEDURES FOR SCHEME 1

(A) Synthesis of 5,7,11-Dodecatriyn-1-ol and 5,7,11,13-Octadecatetrayn-1,18-Diol The above diols were prepared by the Cadiot-Chodkiewicz technique and are used to make the corresponding urethane derivatives. The synthesis is in accordance with the above Scheme 1.

A mixture of 60 parts methanol, 0.15 part cuprous chloride, 40 parts 70% ethylamine in aqueous solution and 1.5 parts of hydroxylamine hydrochloride was prepared. After stirring the contents a short time, 10.9 parts 1,5-hexadiyn (compound 3 of Scheme 1) was added in one portion. The contents were cooled to 15° C., and 25.0 parts 6-bromo-5-hexyn-1-ol (compound 2 of Scheme 1 with x=3) in 16 parts methanol were added dropwise over a period of 20 minutes while maintaining the temperature between 15° C. to 25° C. After stirring for 4 hours the solvent was removed, leaving a dark viscous layer. The triyn-ol was extracted from the reaction mixture by adding 240 parts of petroleum ether (60°–110° C. boiling range) to the reaction mixture, and heating and stirring and decanting the top layer of the mixture. The extraction was repeated twice, and the petroleum ether solutions were refrigerated at −26° C. The triyn-1-ol product formed (compound 4 of Scheme 1 with =3) was a white viscous layer on the bottom of the petroleum ether which was isolated by decanting off the petroleum ether. It was used to form the hexayn diol in Part B below.

The tetrayn-diol also formed (compound 5 of Scheme 1 with x=3) was isolated by adding 50 parts glacial acetic acid to the remaining portion of the reaction contents, heating, and adding 150 parts of hot water while stirring, after which the contents were refrigerated at −8° C. The product tetrayn-diol, crystallized out, was isolated by filtering and then purified by dissolving in 280 parts hot xylene and refrigerating the xylene extract at −8° C. After crystallization and filtration, the product was washed with petroleum ether and dried in a vacuum oven in the dark, to yield 7.5 parts of final product light in color and fluffy in texture. The melting point of this tetrayn-diol was 118.8° to 121.4° C.

(B) Preparation of 5,7,11,13,17,19-Tetracosahexayn-1,24-Diol (Compound 6 with x=3)

A mixture of 2 parts cuprous chloride, 12 parts methanol, and 4 parts N,N,N′,N′-tetramethylethylenediamine was prepared. To this mixture over a period of 15 minutes was added 5,7,11-dodecatriyn-1-ol (produced in Part A above) dissolved in 12 parts methanol, while oxygen was moderately bubbled through the reaction contents. After 1 hour, oxygen flow was stopped and the methanol was distilled leaving a semi-viscous residue. To this was added 100 parts of 3 N hydrochloric acid while stirring, causing product to precipitate. It was collected by filtration, washed once with 25 parts 2 N hydrochloric acid and several times with water. The solid was dissolved in 200 parts xylene and the solution was refrigerated at −8° C. Subsequent crystallization and filtration yielded 6.0 parts of fluffy product, the above hexayne diol, which turns blue in daylight. The melting point of the material was 101.0° to 104.1° C.

EXAMPLES 5 AND 6

The procedure for oxidizing diols (5) and (6) above to the corresponding diacids (7) and (8) wherein x=1, 2, 3 and 4 was essentially the same as for obtaining the diacid of Example 1.

The acids for completely conjugated tetrayns of type,

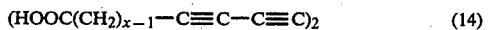    (14)

were obtained by converting the respective diols, as follows in Scheme 2 and in Scheme 3:

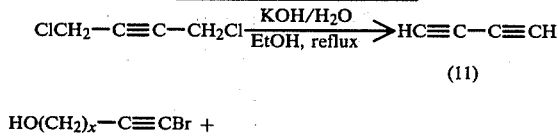

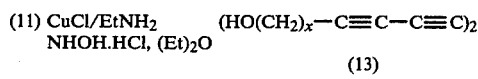

SPECIFIC PROCEDURES FOR SCHEME 2

Preparation of Diacetylene, Compound (11)

The diacetylene was prepared using the method of T. H. Herberts (Chem. Ber., 85 (1952) 475) cited by M. F. Shostakovskii and A. V. Bogdanova ("The Chemistry of Diacetylenes", p. 11). The procedure used is as follows: To a 3-necked 0.5 L flask fitted with a stirrer, condenser, a dropping funnel, and a nitrogen inlet with a tube extending to the bottom of the reaction flask, 48 g (38.2mL, 0.39 mol) 1,4-dichloro-2-butyne, 120 mL ethanol, and 4 mL pyridine were added. The reaction medium was raised to reflux, the nitrogen adjusted so that bubbling occurred very gently and then 160 mL aqueous solution of 10 N NaOH was added dropwise over 1.75 h. During the addition, the diacetylene evolved as gas (B.P., 10° C.) and was directed through the upper arm of the condenser, purified by bubbling through a wash bottle containing a 150 mL aqueous solution of 10 N NaOH, and finally collected, via a dip-tube, at −50° to −70° C. at the bottom of the 3-necked flask described in the following synthesis. Conversion to diacetylene was greater than 95%.

Synthesis of 3,5,7,9-Dodecatetrayn-1,14-Diol (Compound (13) where x=2)

To a 1 L 3-necked flask fitted with a stirrer, thermometer, a dropping funnel, and a nitrogen inlet and outlet 0.4 g CuCl and 300 mL diethylether were added followed by 50 mL ethylamine (70%). After a short period of time 5.0 g hydroxylamine hydrochloride was added while stirring moderately. Afterwards the stirrer was stopped and the medium cooled to −50° to −70° C.

Diacetylene described above was collected at the bottom of this second flask via a dip tube, over a period of 2.25 h and estimated to be approximately 19 g (0.38 mol). The condensation tube was disconnected and the temperature was allowed to rise to −10° C. using a solid carbon dioxide/acetone bath to maintain such temperature.

A solution of 80.0 g (0.536 mol) 4-bromo-3-butyn-1-ol ((2), of Scheme 1 where x=1) diluted with 60 mL diethylether was added dropwise over a period of 0.5 h; a color change from red to brown was noted (Caution: the red color indicates the presence of copper acetylide and therefore a protective shield should be used).

The temperature was then slowly raised 5° C. every 0.5 h until room temperature (25° C.) was obtained. The reaction was continued for an additional 0.5 to 1.0 h; then the mixture was acidified by adding 200 mL 2.8 N HCl slowly and the reaction medium was separated in a separatory funnel saving the ether layer. The inorganic layer was extracted twice with additional ether using 100 mL each time. The combined ether extract was washed with 100 mL water and separated. The ether layer was reduced to 200 mL and 800 mL n-hexane added to precipitate the product. The product was filtered, washed with n-hexane and recrystallized by dissolving in 600 mL warm xylene followed by 1,600 mL n-hexane and cooling at −8° C. Yield after crystallization; 21.8 g of white solid that in daylight turns first green, then blue.

SCHEME 3

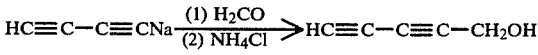

-continued
SCHEME 3

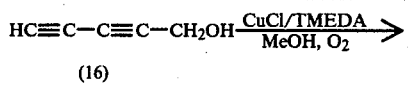

(16)

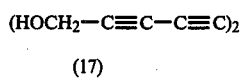

(17)

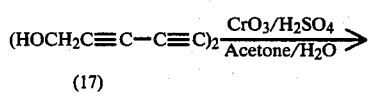

(17)

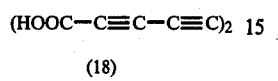

(18)

SPECIFIC PROCEDURES FOR SCHEME 3

Preparation of 2,4,6,8-Decatetrayn-1,10-Diol, Compound (17)

2,4-pentadiyne-1-ol (16) was prepared according to the method of J. B. Armitage, E. R. Jones and M. C. Whiting, J. Chem. Soc. 3317 (1953); and coupled using the method of A. S. Hay (J. Polymer Sci., 7, 1625 (1960)).

EXAMPLES 7-10

The procedure for oxidizing diols (13) of Scheme 2 above wherein x=2, 3, or 4; and for oxidizing diol (17) of Scheme 3 to the corresponding diacids is essentially the same as for obtaining the diacid of Example 1, above.

TECHNIQUES FOR ACTIVATION OF AN INDICATOR BASED ON ION EXCHANGE

In general, not all of the acetylenic acids are transformable to their inactive salts. (Inactive carries the meaning of not undergoing a color change due to polymerization either upon thermal annealing or by irradition, such as indefinitely long exposure at room temperature to daylight). As a consequence two techniques were used to employ the acetylenic acids as indicators of the combined effects due to time and temperature of thermal exposure, or due to time and intensity of irradiation. The first is based on activation of the monomer in salt form by conversion to the acid form, whereas the second is dependent on the characteristic water solubility of the polymeric alkali metal salts.

TECHNIQUE 1

For diacid compounds that formed inactive salts, a 10 to 20% aqueous solution of the disodium salt was prepared by adding to the diacid an equimolar amount of NaOH. The solution was applied to a filter paper substrate and dried, leaving the inactive disodium salt of the diacid on the filter paper.

One-half inch tabs were cut from the coated paper and placed on a layer of microcapsules (commercially available) containing an aqueous citric acid solution. The tab and the capsules were then encased in a polyethylene film. In order to activate the tab, the microcapsules are broken by crushing. The ensuing acid-salt exchange converts the indicator to its active acid form. The color change occurring, as the acid form polymerizes, varies according to the conjugated acetylenic acid which is used. In general, the higher the conjugation, the greater the reactivity and consequently the greater the rate of color change which occurs.

TECHNIQUE 2

For those acids which could not be inactivated by transformation to their sodium salts, the acid form was dissolved in a suitable solvent, e.g. acetone, and applied to a filter paper substrate and converted either by heat or U.V. light to its polymer, colored e.g. blue. Behind the paper substrate a microporous film was placed followed by a wet tab that had been soaked in NaOH. In the wet state sodium ions migrate, at a rate depending on the temperature, through the microporous film to produce a color change on the filter paper, blue to red, as the polymer is converted to its sodium salt. Such device accordingly serves as an indicator of the combined effects of time and temperature exposure, i.e. as a time/temperature indicator. (The rate of migration at constant temperature in general decreases with time, so that it may be desirable in some cases to calibrate the device in the time/temperature region of interest).

If the NaOH tab is dry, no sodium ions migrate and no color change occurs at the filter paper surface carrying the polymer in acid form. For dry NaOH on the tab, activation can be accomplished by incorporation (behind the tab) of water filed microcapsules (commercially available); breaking of the capsules by pressure releases the water to activate the indicator.

MODIFICATION OF TECHNIQUE 1

With certain of the above acetylenic di-salts, the shade changes when the salt form is converted to the acid, as the acid polymerizes. For example, the acid form as it polymerizes may develop a change in shade from light blue to a very dark blue. In terms of perceptual interpretability, the effects may be less than satisfactory. For this reason, in order to bring out better color distinguishability, the color development can be enhanced by employing a colored substrate and incorporating an acid-base pH indicator. Such modification results in the color being initially the combined color of the substrate, plus the color due to the pH sensitive acid-base indicator, plus the color of the inactive time-temperature indicator under basic conditions. Activation by releasing, for instance, a solution of citric acid gives the combined effect of the colored substrate and the acid form of the pH indicator which enhance the perceptibility of the color development of the time-temperature indicator. The system results in color transitions rather than only a color intensification as the color of the polyacetylenic polymeric acid develops.

EXAMPLE 11

An example of the foregoing activation TECHNIQUE 1 is described for (HOOC(CH$_2$)$_3$—C≡C—C≡C—CH$_2$)$_2$, i.e. Compound (7) of Scheme 1, with x=3.

A 1" (25.4 mm) square yellow paper was soaked in an aqueous solution composed of 1 part 0.3% dichlorofluorescein and 1 part of a 10% solution of the disodium salt of the above diacid. Nine ¼" (6.35 mm) diameter circular tabs were cut from the paper and placed in a testing device constructed by equally punching out ¼" (6.35 mm) holes in a 1"×1"×1/16" (25.4×25.4×1.59 mm) polyethylene holder. In each hole, one of the precut tabs was placed. Behind each tab a layer of capsules containing a citric acid solution was placed. The entire construction was sandwiched between two stick-type clear Mylar ® polyester sheets. The test device was left at room temperature and tested by breaking one tab of the set of 9 sequentially for a period of 9 days and observing the results as color development occurred. The results are as follows: Color changes for days 0, 1, 3, 4, 5, 8, 10, 11, 12 were orange, yellow, yellow-green, green, green-blue, medium-blue, dark-blue, dark-blue and dark-blue, respectively, as the diacetylenic acid polymerized.

EXAMPLE 12

An example of the foregoing TECHNIQUE 2 for activation follows.

A ½" (12.7 mm) square white filter paper tab was soaked in a 10% solution of 4,6-decadiyne-1,10-bis(carboxylmethyl urethane), i.e. the product of Example 3 (B). After drying, the tab was developed to a medium blue color by exposure to U.V. light, which polymerized the diacetylenic diacid.

The tab was sealed between a film of clear polyethylene (front) and a microporous film (back) permeable by aqueous solutions, (specifically the product o the Celanese Plastics Company, CELGARD number 5511). A ½" (12.7 mm) square piece of filter paper was soaked in 5 N NaOH and placed behind the microporous film and joined to the sealed tab by enclosing the whole with polyethylene film. The resulting indicator device was left at ambient conditions. After 20 hours the color had changed from a medium blue to a medium orange color.

The color development of this indicator is dependent on the flow rate of the aqueous NaOH through the microporous film at a particular temperature. Therefore, by using microporous films having differing flow rate characteristics, different color development times are achieved under the same temperature exposures.

EXAMPLE 13

A 0.004% solution of polymer of Example 3(D) was made in deionized water. The absorption spectrum of the polymer alone was recorded in a spectrophotometer.

Individual solutions of metal salts of $Cu^{++}$, $Ni^{++}$, $Al^{+++}$, $Co^{++}$, and $Cr^{+++}$ in concentrations of the metal ion from 0.1 to 10 ppm were also made in deionized water. With the same 0.004% polymer concentration maintained, the metal ionic solutions were added individually to the polymer solution; and the spectra of the resulting solutions were recorded.

For $Cu^{++}$, a wide structureless absorption spectrum was produced with a peak at 462 nm. All of the spectra were similar, all showing a regular gradual shift toward the red, with increasing metal ion concentration. Regular growth of a secondary peak at higher wavelength also was observed as the concentration of the given metal ion increased.

The intensity of the primary peak decreases, more and more, as the concentration of the given metal ion increases.

The close similarity of the absorption spectra produced by the polymer with various metal ions allows use of the subject water soluble polymer salts of alkali metals for qualitative and semiquantitative detection of presence of metallic impurities in water, down as low as a parts per billion level, by comparing the spectrum of the unknown plus polymer against the standard spectrum for the polymer alone; without necessarily separating or identifying the individual metallic impurities.

If the unknown is a single metal, its concentration can be determined quantitatively at such levels by comparison of a series of such spectra against a series of standards made up as above, from a solution of polymer, plus solutions of a compound of that metal in varying concentration.

We claim:

1. A polymeric compound prepared by the 1,4 addition of a diacetylenic monomer of the formula $[R(C\equiv C)_a(CH_2)_b(C\equiv C)_{b-1}]_2$ wherein a is 1 or 2 and b is 0 when a is 1; b is 0, 1, or 2 when a is 2 and (b−1) is taken as zero whenever b is zero; wherein R is selected from the group consisting of (I): $-(CH_2)_nO(C=O)NHCH_2CO_2M$, n being an integer from 1 to 10 and M representing an alkali metal or hydrogen; and (II): $-(CH_2)_{n'}CO_2M'$, n' being an integer from 0 to 9 and M' being an alkali metal with the proviso that when a is 1, n' is an integer from 0 to 4.

2. Compound of claim 1 wherein a is 1, b and (b−1) are zero, and R is of formula I with n being 3 or 4.

3. Compound of claim 2 wherein M is potassium or sodium.

4. Compound of claim 2 being a cross-linked and water-insoluble polymer.

5. Polymer of claim 4 wherein M is potassium or sodium.

6. Compound of claim 1 wherein a is 2, b is 1 or 2, and R is a formula II with n' being an integer from 1 to 4.

7. Compound of claim 1 wherein a is 2, b and (b−1) are zero, and R is of formula II with n' being an integer from 1 to 4.

8. Process of ion exchange which comprises contacting an alkali metal salt of a polymer of claim 1 with an aqueous solution of a salt of a metal other than an alkali metal whereupon the salt of said polymer with said other metal precipitates from said aqueous solution.

9. Process of claim 8 wherein said salt of a polymer is the potassium or sodium salt.

10. Process of claim 8 wherein said polymer is formed by the 1,4 addition of a diacetylenic monomer of the formula $[R+C\equiv C)_a(CH_2)_b(C\equiv C)_{b-1}]_2$ wherein a is 1, b is 0, b−1 is 0, and R is of the formula $-(CH_2)_n-O-(C=O)NHCH_2CO_2M$ where n is 3 or 4 with M being an alkali metal or hydrogen.

11. Process of claim 10 wherein the cation of said other metal in the precipitated polymer salt is brought into aqueous solution by contacting the polymer containing the same with aqueous acid; and the alkali metal salt form of the polymer is regenerated from the resulting residue of polymer in acid form by addition thereto of aqueous alkali.

12. A polymer according to claim 1 wherein said polymer is prepared by polymerizing said monomeric compound by irradiation or thermal annealing, which polymerization occurs by 1, 4 addition at one or more conjugated acetylenic functionalities, said polymer having a plurality of functionalities of the formula:

$$+\overset{|}{C}=C=C=\overset{|}{C}+$$

within the polymer chain.

* * * * *